United States Patent [19]

Segall et al.

[11] Patent Number: 5,945,272
[45] Date of Patent: *Aug. 31, 1999

[54] PLASMA EXPANDERS AND BLOOD SUBSTITUTES

[75] Inventors: Paul E. Segall; Harold D. Waitz; Hal Sternberg; Judith M. Segall, all of Berkeley, Calif.

[73] Assignee: BioTime, Incorporated, Berkeley, Calif.

[*] Notice: This patent is subject to a terminal disclaimer.

[21] Appl. No.: 08/886,921

[22] Filed: Jul. 2, 1997

Related U.S. Application Data

[63] Continuation of application No. 08/780,974, Jan. 9, 1997, abandoned, which is a continuation of application No. 08/364,699, Dec. 29, 1994, abandoned, which is a continuation-in-part of application No. 08/253,384, Jun. 3, 1994, Pat. No. 5,702,880, which is a continuation-in-part of application No. 08/133,527, Oct. 7, 1993, abandoned, which is a continuation-in-part of application No. 08/071,533, Jun. 4, 1993, Pat. No. 5,407,428.

[51] Int. Cl.$^6$ .............................. A01N 1/02; A61M 37/00
[52] U.S. Cl. ...................... 435/1.2; 604/4; 435/2
[58] Field of Search ............... 435/1.1, 1.2, 1.3, 435/2; 604/4

[56] References Cited

U.S. PATENT DOCUMENTS

| | | |
|---|---|---|
| Re. 34,077 | 9/1992 | Segall et al. . |
| 3,937,821 | 2/1976 | Irikura et al. . |
| 3,949,098 | 4/1976 | Bangert . |
| 4,001,401 | 1/1977 | Bonsen et al. . |
| 4,061,736 | 12/1977 | Morris et al. . |
| 4,216,205 | 8/1980 | Radowitz . |
| 4,663,166 | 5/1987 | Veech . |
| 4,908,350 | 3/1990 | Kramer et al. . |
| 4,923,442 | 5/1990 | Segall et al. . |
| 4,927,806 | 5/1990 | Kramer et al. . |
| 5,082,831 | 1/1992 | Leaf et al. . |
| 5,084,377 | 1/1992 | Rowan et al. . |
| 5,120,719 | 6/1992 | Iwamoto et al. . |
| 5,130,230 | 7/1992 | Segall et al. . |
| 5,171,526 | 12/1992 | Wong et al. . |
| 5,374,624 | 12/1994 | Segel . |
| 5,407,428 | 4/1995 | Segall et al. . |
| 5,571,801 | 11/1996 | Segall et al. ........................ 514/59 |
| 5,702,880 | 12/1997 | Segall et al. ........................ 435/1.2 |

OTHER PUBLICATIONS

Rosenberg, "Plasma–Substitutes and Artificial Oxygen Carriers" Bibl. Haemat. 38 (II): 737–745 (1971).
Belzer, F.O. et al., (1985) "Combination Perfusion–Cold Storage for Optimum Cadaver Kidney Function and Utilization," *Transplantation* 39:118–121.
Bishop, M.C. and Ross, B.D., (1978) "Evaluation of Hypertonic Citrate Flushing Solution for Kidney Preservation Using the Isolated Perfused Rat Kidney," *Transplantation* 25:235–239.
Collins, G.M., (1969) "Hypothermic Kidney Storage," *Transplantation Proceedings* IX:1529–1534.
Kallerhoff, M. et al., (1985) "Effects of Preservation Conditions and Temperature on Tissue Acidification in Canine Kidneys," *Transplantation* 39:485–489.
Messmer, K. "Characteristics, Effects and Side–Effects of Plasma Substitutes," *Bodensee Symposium on Microcirculation* (Hammersen and Messmer, eds.), Karger, N.Y., pp. 51–70.
Ross, H. et al., (1976) "72–Hr Canine Kidney Preservation Without Continuous Perfusion," *Transplantation* 21:498–501.
Spahn, D.R. et al., (1994) "Cardiovascular and Coronary Physiology of Acute Isovolemic Hemodilution: A review of Nonoxygen–Carrying and Oxygen–Carrying Solutions," *Anesth. Analg.* 78: 1000–1021.
Wall, W.J., (1977) "Simple Hypothermic Preservation for Transporting Human Livers Long Distances for Transplantation," *Transplantation* 23:210–216.
*ATCC Catalogue of Bacteria and Bacteriophages*, (1992) p. 486, Medium 1590.
Lehninger, A. (1982) "Digestion, Transport, and the Integration of Metabolism," *Principles of Biochemistry* Chapter 24, Part III, pp. 705–713.
Wagner et al., (1993) "Pharmacologic and Clinical Considerations in Selecting Crystalloid, Colloidal, and Oxygen–Carrying Resuscitation Fluids," *Clinical Pharmacy* 12:335–346.
Fisher, J.H. et al., (1985) "Flush Solution 2, A New Concept for One–to–Three–Day Hypothermic Renal Storage Preservation," *Transplantation* 39:122–126.
Sprung, J. et al., (1991) "Effects of Acute Hypothermia and β–Adrenergic Receptor Blockade on Serum Potassium Concentration in Rats," *Critical Care Medicine* 19:1545–1551.
Bailes et al., (1990), "The Use of Ultra–profound Hypothermia in a Totally Exsanguinated and Blood–Substituted Canine Model. I," *Cryobiology* 27:622–623.
Elrifai et al., (1990) "The Use of Ultra–profound Hypothermia in a Totally Exsanguinated and Blood–Substituted Canine Model. II," *Cryobiology* 27:622–623.
Boerema et al., "Life Without Blood," *J. Cardiovasc. Surg.* 13: 133–146.
Fischbach, F., "Chemistry Studies: Potassium ($K^+$)," *A Manual of Laboratory Diagnostic Tests*, Third Edition, Chapter 6, pp. 254–257.

(List continued on next page.)

*Primary Examiner*—Sandra E. Saucier
*Attorney, Agent, or Firm*—Bozicevic, Field & Francis LLP; Bret Field

[57] ABSTRACT

A blood substitute solution and methods for its use are provided. The subject solution contains: subphysiological amounts of potassium ion, 0–10 mM magnesium ion, 70–160 mM sodium ion, 0.5–4.0 mM calcium ion, and 80–170 mM chloride ion; one or more water soluble oncotic agents; an organic carboxylic acid or salt thereof; physiological amounts of a sugar; and a blood clotting factor. The subject solution is further characterized in that it does not include a conventional biological buffer. The subject solutions find use in a variety of different applications, e.g. as blood volume expanders, and the like.

20 Claims, No Drawings

OTHER PUBLICATIONS

Smith, A., (1956) "Studies on Golden Hamsters During Cooling to and Rewarming from Body Temperatures Below 0° C.," *Proceedings of the Royal Society* 145:391–442.

Leavitt, et al. (1990) "Survival from Prolonged Cardiac Arrest in Totally Exsanguinated Hypothermic Dogs," *Abstracts: Federation of American Societies for Experimental Biology* Part 2, 4048.

Segall et al., (1987) "Ice–Cold Bloodless Dogs Revived Using Protocol Developed in Hamsters," *Abstracts: Federation of American Societies for Experimental Biology* 5959.

Segall et al., (1991) "Animal Models in Ice–Cold Bloodless Medicine," *Abstracts: The FASEB Journal* Part I, 147.

Sternberg, et al., (1990) "Interventive Gerontology, Cloning and Cryonics," *Biomedical Advances in Aging* Chpt. 19:207–219.

Sternberg, et al., (1991) "Partly–Frozen Overnight, Thawed Hamsters' Hearts Beat," 1991 *FASEB* Abstract Form.

Storey, K.B. and Storey, J.M., (1990) "Frozen and Alive," *Scientific American* 263(6):92–97.

Waitz et al., (1991) "Hamsters Live After Hours of Bloodless Hyperbaric $O_2$," *Abstracts: The FASEB Journal* Part II, 4375.

Bishop et al., (1978) "Evaluation of Hypertonic Citrate Flushing Solution for Kidney Preservation Using the Isolated Perfused Rat Kidney," *Transplantation* 25:235.

"10% LMD in 5% Dextrose Injection . . . ," Product Information Sheet, Abbott Laboratories, North Chicago, IL.

"6% Dextran 70 in 5% Dextrose Injection . . . ," Product Information Sheet, (1987) Abbott Laboratories, North Chicago, IL.

PLASMA EXPANDERS AND BLOOD SUBSTITUTES

CROSS-REFERENCE TO RELATED APPLICATIONS

This application is a continuation of application Ser. No. 08/780,974 filed on Jan. 9, 1997 and now abandoned; which application is a continuation of application Ser. No. 08/364, 699 filed Dec. 8, 1994 and now abandoned; which application is a continuation-in-part of application Ser. No. 08/253, 384 filed Jun. 3, 1994 and now issued as U.S. Pat. No. 5,702,880; which application is a continuation-in-part of application Ser. No. 08/133,527 filed Oct. 7, 1993 and now abandoned; which application is a continuation-in-part of application Ser. No. 08/071,533, filed Jun. 4, 1993 and now issued as U.S. Pat. No. 5,407,428; the disclosures of which applications are herein incorporated by reference.

FIELD OF THE INVENTION

The present invention relates generally to aqueous solutions and methods for using aqueous solutions to perfuse a mammalian subject in need of perfusion and which act as effective substitutes for blood.

BACKGROUND OF THE INVENTION

Two clinically applied preservation methods for organs are known: (1) initial perfusion for about 5 min with subsequent cold storage (2° C.), and (2) continuous perfusion using aqueous solutions.

Many of the solutions used for initial perfusion with subsequent cold storage are based on the solutions of Collins et al. (1969) Lancet 2:1219 and Sacks et al. (1973) Lancet 1:1024 (see also, Ross et al. (1976) Transplantation 21:498, Wall et al. (1977) Transplantation 23:210, Bishop & Ross (1978) Transplantation 25:235, Fischer et al. (1985) Transplantation 39:122, Belzer et al. (1985) Transplantation 39:118, Kallerhoff et al. (1985) Transplantation 39:485, and Klebanoff & Phillips (1969) Cryobiology 6:121).

Segall et al. (U. S. Pat. Nos. 4,923,442 and 5,130,230) describe blood substitute capable of maintaining a subject and its organs at temperatures below 20° C. composed of two to four solutions—a base solution, a cardioplegia-inducing solution, a cardioplegia-maintaining solution, and a recovery solution, with potassium ion concentrations ranging from 4–45 mEq.

SUMMARY OF THE INVENTION

The invention features solutions and methods for their use as plasma expanders and blood substitutes in mammals, including primates.

Accordingly, the invention features a solution to replace all or a portion of the blood of a mammalian subject, including a primate, comprising $K^+$, $Mg^{++}$, $Na^+$, $Ca^{++}$, $Cl^-$; one or more water soluble oncotic agents; an organic carboxylic acid or salt thereof; and physiological levels of a sugar, with the proviso that the solution does not contain a conventional biological buffer.

The solutions of the invention may be used to replace all or a portion of the blood of a mammalian subject, including a primate, at normal temperatures or at temperatures substantially below those normally maintained by a mammal, generally less than 37°–38° C. and greater than −2° C.

In one embodiment, the solution includes one or more water soluble oncotic agents selected from the group consisting of high molecular weight hydroxyethyl starch, low molecular weight hydroxyethyl starch, dextran 70, dextran 40, albumin, and mannitol.

By the term "water soluble oncotic agent" is meant a molecule whose size is sufficient to prevent its loss from the circulation by readily traversing the fenestrations of the capillary bed into the interstitial spaces of the tissues of the body. Examples of water soluble oncotic agents include starches, proteins, and sugars.

The use of blood-free plasma expanders and blood substitutes may result in substantial hemodilution. This is of concern because it may place a subject at risk for hemorrhage. It would be advantageous to administer a blood clotting factor to a subject undergoing blood substitution. Also, when a subject has undergone substantial blood loss and continues to lose blood, it would be advantageous to administer both a blood substitute and a blood clotting factor. Accordingly, one aspect of the invention encompasses blood substitute solutions containing a blood clotting factor. Another aspect of the invention encompass a method of administering a blood substitute followed by or with the simultaneous administration of a blood clotting factor. Preferably, the blood clotting factor is selected from the group consisting of vitamin K, Factors I, II, V, VII, VIII, VIIIC, IX, X, XI, XII, XIII, protein C, von Willebrand factor, Fitzgerald factor (prekallikrein), Fletcher factor (high molecular weight kininogen), and a proteinase inhibitor, such as aprotinin. An example of an aprotinin is Trasylol® (Miles, West Haven, Conn.), a saline solution of aprotinin containing 10,000 Kallikrein-Inhibitor Units (KIU)/ml. By the term "blood clotting factor" is meant a factor which accelerates, promotes, or allows the formation of a blood clot. Preferably, the blood clotting factor is present in an amount that results in a blood concentration in the subject of between 100–100,000 KIU/ml.

Oxygen-carrying solutions have been developed based on hemoglobin from human or animal sources, or made by genetic engineering, and modified by techniques such as crosslinking or the addition of polyethylene glycol (Spahn et al. (1994) Anesth. Analg. 78:1000–1021). However, these solutions are toxic in high quantities. When a subject has lost blood, it would be advantageous to administer a blood substitute with a physiological or hyperphysiological oxygen-carrying capacity. Accordingly, in another aspect, the solution of the invention includes an oxygen-carrying component. When the solution contains an oxygen-carrying component, such as cross-linked or high molecular weight hemoglobin, it may be desirable to reduce the amount of oncotic agent present such that colloid osmotic pressure approximately that of normal human serum, about 28 mm Hg. Preferably, the oxygen-carrying component is selected from the group consisting of hemoglobin or other respiratory pigments extracted from natural sources, such as hemocyanin, chlorocruorin, and hemerythrin, respiratory pigments made by recombinant DNA techniques, a crosslinked form of hemoglobin, and fluorocarbons. The oxygen-carrying component may be modified by methods known to the art, for example, a fluorocarbon component may be encapsulated by a liposome, and respiratory pigments altered by crosslinking or reaction with polyethylene glycol. By the term "oxygen-carrying component" is meant a component which forms an easily reversible interaction with oxygen, which allows more oxygen to be solubilized than would otherwise be possible, and that results in delivery of the excess oxygen to the tissue. A prefered oxygen-carrying component is hemoglobin, present in the concentration range of about between 20–200 g/l.

In a related aspect, the solutions of the invention are useful for harvesting and/or delivering red blood cells to patients in need thereof. Red blood cells for delivery may be obtained from a number of sources, including human donors, transgenic animals, or derived in vitro.

Plasma expanders and blood substitutes having two or more oncotic agents with differential clearance rates are particularly advantageous in providing extensive protection of oncotic pressure without inhibiting the subject's production of replacement plasma proteins. The present invention includes solutions having two or more oncotic agents with differential clearance rates. By the term "differential clearance rates" is meant the rate at which a first oncotic agent is removed from the blood circulation is faster than the rate at which a second oncotic agent is removed.

The solutions of the present invention include physiological levels of a sugar. Preferably, the sugar is a simple hexose sugar such as glucose. By "physiological levels of a sugar" is meant a sugar concentration of between 2 mM to 50 mM. The preferred concentration of glucose is 5 mM.

Particular advantages of the solutions are that they are relatively inexpensive, contain components naturally occurring in the human body or which have been shown to be safe for use in the human body. The solutions of the present invention can be terminally heat sterilized, and can support life when replacing 50%–80% of a subject's blood at normal body temperature, or look of a subject's blood at hypothermic temperatures.

DETAILED DESCRIPTION

It must be noted that as used herein and in the appended claims, the singular forms "a," "an," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

The present invention includes plasma expanders and blood substitutes suitable for use in mammals, including primates. The invention presented herein is in part described in U.S. Ser. No. 08/253,384 filed Jun. 3, 1994, U.S. Ser. No. 08/133,527 filed Oct. 7, 1993, and U.S. Ser. No. 08/071,533, filed Jun. 4, 1993, which applications are incorporated herein by reference. This invention is in part based on the discovery that because of the special species-specific physiology of primates, prior art plasma expanders and blood substitutes containing physiological or hyperphysiological potassium concentrations present disadvantages when used for near ice-cold blood-substitution in primates.

Red blood cells of primates contain high concentrations of potassium ion ($K^+$). When primate blood is stored (as is the case with virtually all blood obtained from blood banks), even low levels of lysis of the red blood cells generally result in high potassium ion concentrations. This is due to release of potassium ion from inside the lysed primate red blood cells into the plasma surrounding the cells. Accordingly, the blood will be hyperkalemic when infused. The increased potassium level can be diffused if blood is infused into patients with sufficient circulating blood since the high potassium ion concentration is diluted. However, the problem increases if primate blood is transfused into a primate which has been perfused with a maintenance solution of the type described in U.S. Pat. Nos. 4,924,442, and 5,130,230, which contain high concentrations of potassium resulting in loading of the primate's tissues with excess potassium. The potassium ion concentration in the transfused blood will not be diluted to safe levels. As a result, cardiac insufficiency may and frequently does occur. Hyperkalemia is also associated with tissue damage resulting from burns, accidents, surgery, chemotherapy, and other physical traumas. The prior art teaches that organ preservation at low temperatures requires the presence of high potassium ion concentrations for the maintenance of tissue integrity.

The solution according to the present invention contains physiological or subphysiological amounts of potassium. Thus, the solution allows for dilution of the potassium ion concentration in stored transfused blood. As a result, high concentrations of potassium ion and potential cardiac arrhythmias and cardiac insufficiency caused thereby can be more easily controlled. These solutions are also useful for purposes of blood substitution and low temperature maintenance of a subject. By "physiological amount of potassium" is meant between 3.5–5 mEq/l $K^+$ (3.5–5 mM), preferably 4–5 mEq/l $K^+$ (4–5 mM). By "subphysiological amount of potassium" is meant between 0–3.5 mEq/l $K^+$ (0–3.5 mM), preferably 2–3 mEq/l $K^+$ (2–3 mM).

The solution of the present invention comprises a mixture of materials which when placed in aqueous solution may be used to perfuse a subject in need thereof. While the materials may be provided as a dry mixture to which water is added prior to heat sterilization or as a dry sterile mixture to which sterile water is added, the solution is preferably provided in the form of a sterile aqueous solution.

The solution of the present invention may be used as a single solution for all phases of procedures in which a subject's blood is removed and replaced or a subject is cooled. Such phases include hemodilution or plasma extension at normal body temperatures, blood replacement and exchange at hypothermic body temperatures, blood substitution at substantially hypothermic body temperatures, and subject warming. "Hypothermic body temperatures" are defined as 3–5° C. below normal body temperatures of 37–38° C., e.g., about 32–35° C. "Substantially hypothermic body temperatures", also referred to as "near-ice cold" temperatures are defined as body temperatures just below the freezing point (−2° C.) to about 10° C. Therefore, the term "hypothermic body temperature" or "hypothermia" as used herein encompasses body temperatures of about −2 to 3° C. to about 32–35° C.

The solution of the present invention does not include a conventional biological buffer. By "conventional buffer" is meant a compound which in solution, in vitro, maintains pH at a particular range. By "conventional biological buffer" is meant a compound which in a cell-free system maintains pH in the biological range of 7–8. Examples of conventional biological buffers include N-2-Hydroxyethylpiperazine-N'-2-hydroxypropanesulfonic acid (HEPES), 3-(N-Morpholino) propanesulfonic acid (MOPS), 2-([2-Hydroxy-1,1-bis(hydroxymethyl)ethyl]amino)ethanesulfonic acid (TES), 3-[N-tris(Hydroxy-methyl) ethylamino]-2-hydroxyethyl]-1-piperazinepropanesulfonic acid (EPPS), Tris[hydrolymethyl]-aminomethane (THAM), and Tris [Hydroxylmethyl]methyl aminomethane (TRIS) Conventional biological buffers function independently of normal biological processes, e.g., the conventional buffer is not metabolized in vivo, and are most potent in cell-free systems.

The solution of the present invention uses normal biological components to maintain in vivo biological pH, a concept termed a "dynamic buffering system". The dynamic buffering system concept rests on the discovery by the inventors that compounds with no intrinsic buffering capacity in the biological range, such as lactate, acetate, or gluconate, capable of being metabolized in vivo, act with other solution components to maintain a biologically appropriate pH in an animal, even at hypothermic temperatures and at essentially bloodless conditions. The dynamic buffering system of the present invention depends in part on oxygenation and removal of carbon dioxide ($CO_2$); and allows but does not require additional bicarbonate ($NaHCO_3$) The dynamic buffer of the invention has no or substantially no ability to act as a buffer outside of a biological system, i.e., a dynamic buffer maintains pH in the biological range in vivo but not in a cell free environment.

A component of the dynamic buffering system of the invention include a carboxylic acid, salt or ester thereof. What is meant by a carboxylic acid, salt or ester thereof is a compound having the general structural formula RCOOX, where R is an alkyl, alkenyl, or aryl, branched or straight chained, containing 1 to 30 carbons which carbons may be substituted, and preferably one of the carbon chains that compose the carbon chain of lactate, acetate, gluconate, citrate, pyruvate, or other biological metabolites; and X is hydrogen or sodium or other biologically compatible ion substituent which can attach at the oxygen position.

The absence of a conventional biological buffer in the solution of the invention confers several important medical advantages. For example, lower concentrations of buffers consisting of normal biological components are required to maintain in vivo pH, compared to conventional biological buffers. Conventional biological buffers may also pose toxicity problems. Further, the absence of a biological buffer allows the solution to be terminally heat sterilized. Generally, medical solutions are preferred to be terminally heat sterilized prior to use in a patient. The term "terminally heat sterilized" or "heat sterilized" as used herein references to the process involving heating a solution to 120° C. for 15 minutes under pressure, i.e., maintaining heat and pressure conditions for a period of time sufficient to kill all or substantially all bacteria and inactivate all or substantially all viruses in the solution. This procedure is normally performed in an autoclave, and is also known as "autoclaving". The purpose of heat sterilization is to kill possible infectious agents present in the solution. Infectious agents are known to tolerate temperatures up to 100° C. It is generally considered by the art that heating a solution under pressure to 120° C. for about 15 minutes is sufficient to insure sterility. Governmental regulations may require heating a solution at even higher temperatures and pressures.

Transplant or blood substitute solutions containing proteins or a variety of organic compounds of which the inventors are aware cannot tolerate terminal heat sterilization at high temperatures and pressures. It is known that heat sterilizing a solution having containing carbohydrates or proteins, with a pH above 7.0, results in substantial degradation of solution components.

By contrast, the solution of the present invention is designed to be heat sterilizable with minimal degradation of other solution components, such as sugar. The solutions of the present invention are heat sterilized prior to use. When it is desirable to add components to the base solution, e.g., addition of $NaHCO_3$ to HL solution to form HLB solution for use under hypothermic conditions, $NaHCO_3$ is added as a commercially-available sterile 1 M solution to sterile HL solution. Generally, 5 ml of a 1 M $NaHCO_3$ solution is added per liter of HL solution to form 1 l of HLB solution. However, more $NaHCO_3$ may be added. Similarly, when it is desirable to add a blood clotting factor or oxygen-carrying component, the blood clotting factor or oxygen-carrying component is added as a sterile solution to the autoclaved base solution.

The HLB solution of the present invention, or its buffering organic acids and salts, may also be used to sustain cultured tissues and cells in vitro. The dynamic buffering system of the solution maintains cultured tissues and cells at the appropriate biological pH. We have shown that the addition of lactate and bicarbonate to cultured cells is sufficient to sustain normal cell growth and morphology.

The solution of the present invention includes an organic carboxylic acid or salt thereof. The term "organic carboxylic acid or salt thereof" includes any carboxylic acid or carboxylic acid derivative capable of being metabolized by the mammal. Examples of carboxylic acids and carboxylic acid salts suitable for use in the solution of the present invention include lactate and sodium lactate, citrate and sodium citrate, gluconate and sodium gluconate, pyruvate and sodium pyruvate, succinate and sodium succinate, and acetate and sodium acetate. In the following Examples describing the use of HLB solution, sodium lactate is used. When metabolized in vivo, lactate helps maintain bicarbonate levels, and thereby functions as a component of the dynamic buffering system of the solution to maintain an in vivo biological pH.

For purposes of the further description of the invention, the mixture according to the invention will be discussed as an aqueous solution. From the following description of the invention, it is expected that one ordinarily skilled in the art would be enabled to provide the mixture as a dry mixture and make the adjustments to amounts of sodium chloride and organic salt of sodium as necessary to accommodate the amounts of sodium chloride found in normal saline solution, which may be used as a diluent for the dry mixture according to the invention.

The sodium ion concentration is preferably in a range from 70 mM to about 160 mM, and preferably in a range of about 130 to 150 mM.

The concentration of calcium ion is in a range of about 0.5 mM to 4.0 mM, and preferably in a range of about 2.0 mM to 2.5 mM.

The concentration of magnesium ion is in a range of 0 to 10 mM, and preferably in a range of about 0.3 mM to 0.45 mM. It is important not to include excessive amounts of magnesium ion in the solution according to the invention because high magnesium ion concentrations negatively affect the strength of cardiac contractile activity.

The concentration of chloride ion is in the range of 80 mM to 170 mM, preferably in the range of 110–135 mM $Cl^-$.

The solution also includes a physiological amount of simple hexose sugar such as glucose, fructose and galactose, of which glucose is preferred. In the preferred embodiment of the invention nutritive hexose sugars are used and a mixture of sugars can be used. The term "physiological amount" or "physiological levels" means the concentration of sugar is in a range between 2 mM and 50 mM with concentration of glucose of 5 mM being preferred. At times, it is desirable to increase the concentration of hexose sugar in order to lower fluid retention in the tissues of a subject. Thus the range of hexose sugar may be expanded up to about 50 mM if necessary to prevent or limit edema in the subject under treatment.

The oncotic agent is comprised of molecules whose size is sufficient to prevent their loss from the circulation by readily traversing the fenestrations of the capillary bed into the interstitial spaces of the tissues of the body. As a group, oncotic agents are exemplified by blood plasma expanders. Examples of oncotic agents suitable for use in the solution of the present invention include human serum albumin, polysaccharides such as glucan polymers, and cross-linked or high molecular weight hemoglobin. Preferably, the polysaccharide is non-antigenic.

Hetastarch (McGaw, Inc.) is an artificial colloid derived from a waxy starch composed almost entirely of amylopectin with hydroxyethyl ether groups introduced into the alpha (1→4) linked glucose units. The colloid properties of a 6% solution (wt/wt) of Hetastarch approximates that of human serum albumin. Other polysaccharide derivatives may be suitable as oncotic agents in the solutions according to the invention including hydroxymethyl alpha (1→4) or (1→6) polymers. Cyclodextrins are suitable oncotic agents.

D-glucose polymers may be used. For example, dextran, which is D-glucose linked predominantly in alpha (1→6) linkage, may be used as the oncotic agent in the solution of the invention. Polysaccharides such as dextran in a molecular weight range of 30,000 to 85,000 daltons (D) are preferred.

The concentration of the polysaccharide is sufficient to achieve (when taken together with chloride salts of sodium, calcium and magnesium, organic ion from the organic salt of sodium and hexose sugar discussed above) colloid osmotic pressure approximating that of normal human serum, about 28 mm Hg.

In one aspect of the invention, the solution contains two or more oncotic agents with differential clearance rates. Natural colloids, such as plasma proteins and human serum albumin, are useful for restoration of blood oncotic agent in a hypovolemic patient. However, natural colloids are expensive and in short supply. Also, they cannot be terminally sterilized at high temperatures and pressures. Recombinant human albumin is under development, and may pose less of a threat in transmitting a pathogenic vector. However, this may also prove expensive to produce, and may present difficulties for sterilization and purity. Use of artificial colloids overcome these deficiencies, with the important advantage of lessening the risk of transmitted disease. The solutions of the present invention having two or more oncotic agents with differential clearance rates provide additional advantages in restoring blood oncotic pressure in a hypovolemic subject over an extended period of time, while encouraging the subject's own production of plasma proteins. Artificial oncotic agents with relatively slow clearance rates include high molecular weight Hetastarch (molecular weight 300,000–1,000,000) and dextran 70, measured to have intravascular persistence rates of 6 hours (Messmer (1989) Bodensee Symposium on Microcirculation (Hammersen & Messmer, eds.), Karger, N.Y., pg. 59). Artificial oncotic agents with relatively fast clearance rates include low molecular weight Hetastarch (average molecular weight 40,000–200,000) and dextran 40, having intravascular persistence rates of 2–3 hours (Messmer (1989) supra).

The solution may be used as a circulating solution in conjunction with oxygen or hyperbaric oxygen at normal body temperatures, or with or without hyperbaric oxygen in subjects during procedures. The solution may also be used as a circulating solution in subjects during procedures when the subject's body temperature is reduced significantly below the subject's normal temperature. When warm-blooded subjects are exposed to low temperature conditions during surgical procedures, it is generally desirable to replace the subject's blood with the cold circulating solution of the invention, or the solution circulated for a time, designed to perfuse and maintain the subject and its organs intact during the procedure.

A subject undergoing blood substitution with the blood substitute of the present invention may be at risk for hemorrhage due to hemodilution. Under those circumstances, it is advantageous to administer to the subject a blood clotting factor. Under emergency conditions when a subject has lost a considerable amount of blood and is continuing to bleed profusely, it is advantageous to administer a blood substitute solution and a blood clotting factor with or following administration of the blood substitute. The solutions of the present invention may include a blood clotting factor able to accelerate or promote the formation of a blood clot. The invention further encompasses a method of using the solutions of the present invention with administration of a blood clotting factor to a subject in need thereof. Preferred blood clotting factors for use in the solution of the invention include vitamin K, Factors I, II, V, VII, VIII, VIIIC, IX, X, XI, XII, XIII, protein C, von Willebrand factor, Fitzgerald factor, Fletcher factor, and a proteinase inhibitor. The concentration of the blood clotting factor is determined by one skilled in the art depending on the specific circumstances of treatment. For example, generally when vitamin K is administered, its concentration will be sufficient to deliver 5–10 mg to the patient.

Oxygen-carrying compounds have been studied as a means for increase the oxygen-carrying capacity of a subject. However, oxygen-carrying compounds in an effective amount have been shown to be toxic to the recipient subject. For example, administration of hemoglobin may result in kidney toxicity, stimulation of febrile and immunogenic responses, and stimulation of bacterial growth. Administration of an effective amount of a fluorocarbon may interfere with lung function. The solutions of the present invention may include an oxygen-carrying component in a concentration sufficiently low so as not to be toxic to the subject. Oxygen-carrying components include hemoglobin extracted from human and non-human sources, recombinant hemoglobin, hemocyanin, chlorocruorin and hemerythrin, and other naturally occurring respiratory pigments extracted from natural sources or made by recombinant DNA or in vitro methods. These compounds may be modified by a number of means known to the art, including by chemical crosslinking or pegylation.

The solutions of the present invention may include a sufficient amount of oxygen-carrying component to deliver enhanced oxygen to the tissues of a subject without resulting in toxicity to the subject. A "sufficient amount" of an oxygen-carrying component is an amount allowing a resting subject with an unimpaired circulation and physiology to survive and recover from trauma, illness or injury. In normal humans at normal body temperature, this is at least 5–6 ml $O_2$/100 ml of intravascular fluid. When the oxygen-carrying component is hemoglobin, it is preferably present in the concentration range of between about 20–200 g/l. The solution may be used in a variety of surgical settings and procedures. It may be useful in delicate neurosurgery where clear surgical fields are imperative and reduced central nervous system activity may be desirable and achieved by performing the procedure on a patient whose core temperature and/or cerebral temperature has been substantially reduced. The solution may be used to maintain a subject (which has lost a significant amount of blood, e.g. 20% to 98% of its blood) at normal body temperatures in a pressurized environment at increased oxygen concentration above atmospheric oxygen tension up to 100% oxygen. The subject is maintained in a high oxygen concentration until enough blood components can be synthesized by the subject to support life at atmospheric pressure and oxygen concentration. The solution according to the invention may be used to maintain a subject at temperatures lower than normal body temperature and at a reduced rate of metabolism after traumatic life threatening injury until appropriate supportive or corrective surgical procedures can be performed. In addition the solution may be used to maintain a patient having a rare blood or tissue type until an appropriate matching donor can be found and replacement blood units or other organ can be obtained.

The procedure for replacing substantially all of a mammalian subject's circulating blood may be carried out with the mammalian subject's body temperature being maintained at its substantially normal temperature. In addition the procedure may be carried out with cooling of the subject and reduction of the mammalian subject's body temperature below that of its normal temperature. Cooling may be accomplished by chilling the subject in an ice bath, ice-salt slurry, or cooling blanket. The subject may be further cooled by chilling the solution according to the invention prior to perfusing the subject with the solution.

The solution is also suitable for use for plasmapheresis. Plasmapheresis is a process in which all or a portion of the blood plasma is replaced while one or more groups of formed elements such as red blood cells or lymphocytes are retained. The blood plasma is removed by methods such as centrifugation or filtration. The procedure allows removal of autoantibodies and other toxic agents. The solution of the invention may be used to replace the plasma fraction of the blood during the plasmapheretic procedure. This presents several distinct advantages. Blood plasma cannot be terminally sterilized at high temperatures and pressures. Moreover, plasma is expensive and is sometimes unavailable. In some cases, it can provoke hypersensitivity reactions in patients. These problems are overcome by replacement of all or a portion of the removed plasma with the solutions of the present invention. The solutions of the present invention are also suitable for use in lowering the body temperature of an organ or tissue donor, and as a blood replacement in organs and tissues harvested, stored, or transported for transplantation.

The following Examples are intended to illustrate the invention and its use, and are not intended by the inventors to be limiting of the invention.

EXAMPLES

The following example is put forth so as to provide those of ordinary skill in the art with a complete disclosure and description of how to carry out the synthesis of the invention and is not intended to limit the scope of what the inventors regard as their invention. Efforts have been made to ensure accuracy with respect to numbers used (e.g., amounts, temperature, etc.), but some experimental error and deviation should be accounted for. Unless indicated otherwise, parts are parts by weight, molecular weight is weight average molecular weight, temperature is in degrees Centigrade, and pressure is at or near atmospheric.

Example 1

Solution Compositions

Composition of L solution. The composition of L solution is as follows: $Na^+$ 143 mM; $Ca^{++}$ 2.5 mM; $Mg^{++}$ 0.45 mM; $K^+$ mM 3.0; $Cl^-$ 124 mM; glucose 5 mM; and lactate 28 mM. The solution is filtered to remove undissolved material and placed in autoclavable containers and heated in an autoclave to a temperature of 120° C. for 15 minutes.

Composition of HL (BioTime Hextend™-lactate) Solution. To each liter of L solution, 60 g of high molecular weight Hetastarch is added. HL solution is filtered and heat sterilized after the addition of Hetastarch.

Composition of HLB (BioTime Hextend™-lactate-bicarbonate) Solution. To each heat sterilized liter of HL solution is added 5 ml of a sterile 1 M solution of $NaHCO_3$, medical grade, forming HLB solution Composition of HL-DL (BioTime Hextend™-dextran-lactate) Solution. DL solution was prepared with a concentration of constituents identical to HL except 6% Dextran 40 is used in place of 6% Hetastarch. DL-HL solution was prepared by mixing an equal amount of DL and HL solutions.

Composition of AL (BioTime Albextend) Solution. AL solution is prepared by adding 5% sterile albumin to sterilized L solution. ALB solution is prepared by adding 5 ml of a sterile 1 M solution of $NaHCO_3$ to each liter of AL solution.

Composition of HL-Heme Solution. To sterile HL solution is added 20–200 g/l hemoglobin.

Example 2

Blood Replacement with HL-DL Solution

A 240 g female rat was anesthetized with ketamine, xylazine an acepromazine mixture injected i.m. The animal was placed on a stage and its right femoral artery and vein cannulated. The animal was perfused isovolemically with 10 ml of HL-DL solution until its hematocrit reached 17.2%. The cannulas were removed, vessels ligated, and the incision closed. The animal tolerated perfusion well, and was active and eating within 3 days of the procedure. The animal remains alive and healthy.

Example 3

Reviving An Ice-Cold Blood-Substituted Dog

A 26.8 kg male dog was anesthetized with nembutal and intubated. It was moved to the operating room, ventilated, and catheterized with venous, Foley, arterial, and Swan-Ganz catheters, and after i.v. heparin, its right femoral artery and vein were cannulated. An esophageal tube was inserted and antacid administered. Temperature sensors were placed in the esophagus and the rectum. Methyl prednisolone was injected i.v.

The animal was wrapped in a cooling blanket, and surface cooling initiated. The animal's cannulas were connected to a bypass circuit, which consisted of a vortex blood pump, an oxygenator with a built-in heat exchanger, a secondary in-line heat exchanger, and a funnel for the rapid administration of blood and blood substitute. Whole blood (225 ml) was removed from the dog and saved for rewarming. Blood volume was quickly replaced with HLB solution. The bypass circuit containing 1.05 liters of HLB solution was opened to the animal, and core cooling began.

Thirty three liters of HLB solution were exchanged. By the time the ice-point was approached, the hematocrit was far below 1%. The animal's deep esophageal temperature was below 10° C. for 4 hours and 5 minutes, with a minimum recorded temperature of 0.7° C.

Following the hypothermic period, the animal was warmed. When body temperature climbed past 10° C., venous effluent and whole blood previously collected, as well as donor blood, was returned to the circuit; hematocrit increased with increasing temperature. Lidocaine and bicarbonate were administered, the heart defibrillated, and ventilation begun. When blood pressure and body temperatures approached normal, the animal was weaned from bypass, and protamine and Lasix injected. Several hours after warm-up, the animal was conscious and responsive. The animal remained alive and healthy after the procedure.

Example 4

Reviving an Ice-Cold Blood-Substituted Baboon

A 24 kg male baboon of the species *Papio annubis* was anesthetized first with ketamine and acepromazine i.m., then with i.v. pentothal. It was then immobilized with pancuronium bromide. It was intubated, ventilated, and catheterized with venous, Foley, and arterial catheters. The animal was wrapped in a cooling blanket, and surface cooling initiated. After i.v. heparin was administered, the baboon's right femoral artery and bilateral femoral veins were cannulated. Temperature sensors were placed in the esophagus, rectum and brain. The animal was instrumented for EKG, somatosensory evoked potentials (SSEPs) and EEG. Dexamethazone was injected i.v.

The animal's cannulas were connected to a bypass circuit, which consisted of a vortex blood pump, an oxygenator with a built-in heat exchanger, and a funnel for the rapid administration of blood and blood substitute. Whole blood (300 ml) was removed from the baboon and saved for rewarming. The volume was quickly replaced with 300 ml of physiological saline solution. The bypass circuit, containing 2 liters of Plasmalyte (commercially available electrolyte solution), was opened to the animal and core cooling begun.

After the deep esophageal temperature declined below 13° C., another 2 liters of Plasmalyte containing 12.5 g of mannitol, was added to the circuit, replacing the mixture of blood and Plasmalyte which previously filled the circuit. This diluted blood was saved for use during warming. Immediately afterwards, 10 liters of HLB solution were added, replacing the Plasmalyte. By the time the ice-point was reached, the hematocrit was far below 1%. When the animal reached brain temperature of 3.4° C. and deep esophageal temperature of 2.8° C., the blood pump was stopped and the animal was maintained under a condition of circulatory arrest (standstill) for 45 minutes. After this period, circulation was resumed.

Following the hypothermic period, 4.2 liters of HLB solution were flushed through the animal while collecting venous effluent, and the animal warmed. When body temperature reached 15° C., 2 liters of Plasmalyte were added to the circuit to replace the HLB solution. Mannitol (6.25 g/l) was added to the Plasmalyte in the circuit. Additionally, venous effluent and whole blood previously collected, as well as donor blood cells and fresh-frozen plasma, were returned to the circuit; the animal's hematocrit increased with increasing body temperature. Another 12.5 g of mannitol were added to the circuit. When the esophageal and rectal temperatures approached normal, the heart fibrillated during warming and began beating. Ventilation was begun. When blood pressure and body temperatures approached normal, the animal was injected with protamine i.v., weaned from bypass, its cannulas and catheters removed, and its incisions closed.

The animal's deep esophageal temperature had been below 15° C. for 3 hours, and below 10° C. for 2 hours 17 minutes, with a minimum recorded temperature of 2.8° C. (Table 3). The following morning, the animal was able to sit erect in its cage and pick up and eat pieces of banana, as well as drink apple juice. It remained alive and well until sacrificed more than one week later for histological evaluation.

Example 5

Blood Replacement with Two Solution System in a Patient Undergoing Cardiopulmonary Bypass Surgery A patient is anesthetized, cannulated and instrumented for cardiopulmonary bypass. The patient is wrapped in a cooling blanket and surface cooled to 30° C. The patient is then placed on bypass with the circuit primed with ALB solution. The patient is core and surface cooled until his deep esophageal temperature reaches 20° C. Blood is collected with 4 L of ALB solution, and immediately replaced with HLB solution. The body is then cooled and maintained while surgical procedures and performed on the heart or brain. The patient is then warmed, and the HLB solution replaced first with ALB solution, and then with the AL-blood solution originally removed. 5–10 mg of vitamin K is administered.

One of the advantage of using the ALB solution as a bypass prime and for blood collection is that when the patient's own hemodiluted blood is reinfused during warm-up, albumin functions as the naturally-occurring compound, maintaining blood oncotic agent without impeding the patient's own ability to synthesize albumin.

Example 6

Emergency Blood-Substitution of Hemorrhaging Subject with HL-Heme Solution.

A patient suffering from severe blood loss is infused with HL solution containing 5 mg/l of blood-clotting factor vitamin K and 30 g/l of the oxygen-carrying component hemoglobin. The patient's blood pressure is stabilized and normal oxygen delivery to the patient's tissues is resumed. The patient's body gradually clears the Hetastarch component while synthesizing its own albumin such that blood oncotic pressure remains stabilized during the recovery period.

Use of HL solution containing blood-clotting factors and oxygen-carrying components allows the use of substitute blood to be reduced or completely avoided.

Example 7

Use of Blood Clotting Factor in Hemodiluted Mammals

Six young female rats (227–262 g) were anesthetized, their right femoral arteries and veins cannulated, and 40–60% of their blood replaced with HL solution. After hematocrits were reduced to 16–22%, the animals were slowly injected i.v. with 6 ml of Trasylol® (10,000 KIU/ml). Their tails were severed 30 mm above the tip. Blood loss averaged 0.39±0.06 (mean ±SEM) ml, and all but one animal survived at least one day. Eight control animals were similarly perfused with HL solution, but were not given Trasylol® injections. The average blood loss was 4.8±0.54 ml, and only 3 of the 8 animals survived. Compared to untreated controls, mortality (P<0.02) and blood loss (P<0.002) in the HL-treated animals without Trasylol® was significantly greater.

What is claimed is:

1. A blood substitute solution comprising:

subphysiological amounts of potassium ion, 0–10 mM magnesium ion, 70–160 mM sodium ion, 0.5–4.0 mM calcium ion, and 80–170 mM chloride ion;

one or more water soluble oncotic agents;

an organic carboxylic acid or salt thereof;

physiological amounts of a sugar; and a blood clotting factor;

with the proviso that said solution does not contain a conventional biological buffer.

2. The solution of claim 1, wherein said physiological amounts of a sugar are between about 2.0 mM to 50 mM.

3. The solution of claim 1 wherein said blood clotting factor is vitamin K.

4. The solution of claim 1 wherein said oncotic agents comprise first and second oncotic agents, wherein said first and second oncotic agents have differential clearance rates.

5. The solution of claim 1 wherein said oncotic agents are selected from the group consisting of hydroxyethyl starch, albumin, dextran 70, dextran 40, and mannitol.

6. The solution according to claim 1, wherein said potassium is present in an amount ranging from about 0–3.5 mM.

7. A blood substitute solution comprising:

0–5 mM potassium ion, 0.3–0.45 mM magnesium ion, 70–160 mM sodium ion, 0.5–4.0 mM calcium ion, and 80–170 mM chloride ion;

one or more water soluble oncotic agents;

an organic carboxylic acid or salt thereof;

physiological amounts of a sugar; and a blood clotting factor;

with the proviso that said solution does not contain a convention biological buffer.

8. The solution of claim 7, wherein said physiological amounts of a sugar are between about 2.0 mM to 50 mM.

9. The solution of claim 7, wherein said blood clotting factor is vitamin K.

10. The solution of claim 7 wherein said oncotic agents comprise first and second oncotic agents, wherein said first and second oncotic agents have differential clearance rates.

11. The solution of claim 7 wherein said oncotic agent is selected from the group consisting of hydroxyethyl starch, albumin, dextran 70, dextran 40, and mannitol.

12. The solution according to claim 7, wherein said potassium ion is present in an amount ranging from about 0–3.5 mM.

13. An aqueous blood substitute solution comprising:

0–5 mM $K^+$;

70–160 mM $Na^+$;

0.3–45 mM $Mg^{++}$;

2.0–2.5 mM $Ca^{++}$;

80–170 mM $C^-$;

2–50 mM of a hexose sugar;

a water soluble oncotic agent;

a blood clotting factor; and lactate in a concentration sufficient to provide in vivo buffering in a physiological range;

with the proviso that said aqueous blood substitute solution does not include a conventional biological buffer.

14. The solution according to claim 13, wherein said $K^+$ is present in an amount ranging from about 0–3.5 mM.

15. The solution according to claim 13, wherein said blood clotting factor is vitamin K.

16. The solution according to claim 13, wherein said oncotic agent is selected from the group consisting of hydroxyethyl starch, albumin, dextran 70, dextran 40, and mannitol.

17. An aqueous blood substitute solution comprising:

0–5 mM $K^+$;

70–160 mM $Na^+$;

0.3–45 mM $Mg^{++}$;

2.0–2.5 mM $Ca^{++}$;

80–170 mM $Cl^-$;

an oncotic agent in a concentration sufficient to provide a colloid osmotic pressure of about 28 mm Hg in said solution;

a hexose sugar selected from the group consisting of glucose, fructose and galactose;

an organic carboxylic acid, salt or ester thereof selected from the group consisting of lactate, acetate, citrate, gluconate, pyruvate and succinate in a concentration sufficient to provide in vivo buffering in a physiological range;

with the proviso that said aqueous blood substitute solution does not include a conventional biological buffer.

18. The solution according to claim 17, wherein said $K^+$ is present in an amount ranging from about 0–3.5 mM.

19. The solution according to claim 17, wherein said blood clotting factor is vitamin K.

20. The solution according to claim 17, wherein said oncotic agent is selected from the group consisting of hydroxyethyl starch, albumin, dextran 70, dextran 40, and mannitol.

* * * * *